US00PP28638P3

(12) United States Plant Patent
Wain

(10) Patent No.: US PP28,638 P3
(45) Date of Patent: Nov. 14, 2017

(54) ***CHRYSANTHEMUM* PLANT NAMED 'FIDMERBROBIMP'**

(50) Latin Name: *Chrysanthemum×morifolium*
Varietal Denomination: Fidmerbrobimp

(71) Applicant: Peter Wain, Locks Heath (GB)

(72) Inventor: Peter Wain, Locks Heath (GB)

(73) Assignee: Dümmen Group B.V., De Lier (NL)

( * ) Notice: Subject to any disclaimer, the term of this patent is extended or adjusted under 35 U.S.C. 154(b) by 51 days.

(21) Appl. No.: 14/757,069

(22) Filed: Nov. 11, 2015

(65) Prior Publication Data

US 2017/0135271 P1 May 11, 2017

(51) Int. Cl.
*A01H 5/02* (2006.01)

(52) U.S. Cl.
USPC ..... Plt./290

(58) Field of Classification Search
USPC ..... Plt./290, 287
See application file for complete search history.

(56) References Cited

PUBLICATIONS

Epoch Converter Week Numbers for 2015, retrieved on Feb. 22, 2017, retrieved from the Internet at <http://www.epochconverter.com/weeks/2015> 3 pp.*
Michell's availability list 2015 retrieved on Feb. 22, 2017, retrieved from the Internet at <http://www.michells.com/availabilities/Fidesavailability.pdf> p. 7.*
Raker 2016 Mum-Aster-Daisy retrieved on Feb. 22, 2017, retrieved from the Internet at <http://www.raker.com/doc/2016.raker.mum.aster.daisy.pdf> cover page, pp. 6-7.*

* cited by examiner

*Primary Examiner* — June Hwu
(74) *Attorney, Agent, or Firm* — C. A. Whealy

(57) ABSTRACT

A new and distinct cultivar of *Chrysanthemum* plant named 'Fidmerbrobimp', characterized by its upright to outwardly spreading and uniformly mounded plant habit; moderately vigorous to vigorous growth habit; freely branching habit; dense and full plant form; uniform and freely flowering habit; medium-size decorative-type inflorescences with orange bronze-colored ray florets; mid-season flowering habit; and good garden performance.

1 Drawing Sheet

Botanical designation: *Chrysanthemum×morifolium.*
Cultivar denomination: 'FIDMERBROBIMP'.

BACKGROUND OF THE INVENTION

The present invention relates to a new and distinct *Chrysanthemum* plant, botanically known as *Chrysanthemum×morifolium*, commercially grown as a garden *Chrysanthemum* plant and hereinafter referred to by the name 'Fidmerbrobimp'.

The new *Chrysanthemum* plant is a product of a planned breeding program conducted by the Inventor in Fareham, Hampshire, United Kingdom. The objective of the breeding program is to create new early to mid-season flowering garden *Chrysanthemum* plants with numerous attractive inflorescences.

The new *Chrysanthemum* plant originated from a cross-pollination made in January, 2011 by the Inventor in Fareham, Hampshire, United Kingdom of a proprietary selection of *Chrysanthemum×morifolium* identified as code number G0004, not patented, as the female, or seed, parent with a proprietary selection of *Chrysanthemum×morifolium* identified as code number 83524, not patented, as the male, or pollen, parent. The new *Chrysanthemum* plant was discovered and selected by the Inventor as a single flowering plant from within the progeny of the stated cross-pollination in a controlled greenhouse environment in Fareham, Hampshire, United Kingdom in September, 2011.

Asexual reproduction of the new *Chrysanthemum* plant by terminal vegetative cuttings was first conducted in Fareham, Hampshire, United Kingdom in December, 2011. Asexual reproduction by terminal vegetative cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Fidmerbrobimp'. These characteristics in combination distinguish 'Fidmerbrobimp' as a new and distinct *Chrysanthemum* plant:

1. Upright to outwardly spreading and uniformly mounded plant habit.
2. Moderately vigorous to vigorous growth habit.
3. Freely branching habit; dense and full plant form.
4. Uniform and freely flowering habit.
5. Medium-size decorative-type inflorescences with orange bronze-colored ray florets.
6. Mid-season flowering habit, grown under natural season conditions, plants flower in early to mid-September in the United Kingdom.
7. Good garden performance.

Plants of the new *Chrysanthemum* can be compared to plants of the female parent selection. Plants of the new *Chrysanthemum* differ from plants of the female parent selection in the following characteristics:

1. Plants of the new *Chrysanthemum* are more mounding than and not as upright as plants of the female parent selection.
2. Plants of the new *Chrysanthemum* and the female parent selection differ in ray floret color as plants of the female parent selection have inflorescences with golden bronze-colored ray florets.

Plants of the new *Chrysanthemum* can be compared to plants of the male parent selection. Plants of the new *Chrysanthemum* differ from plants of the male parent selection in ray floret color as plants of the male parent selection have inflorescences with pink-colored ray florets.

Plants of the new *Chrysanthemum* can be compared to plants of *Chrysanthemum×morifolium* 'Daybreak Dark Bronze', not patented. In side-by-side comparisons conducted in Fareham, Hampshire, United Kingdom, plants of the new *Chrysanthemum* differed from plants of 'Daybreak Dark Bronze' in the following characteristics:

1. Grown under natural season conditions, plants of the new *Chrysanthemum* flowered later than plants of 'Daybreak Dark Bronze'.
2. Plants of the new *Chrysanthemum* had larger inflorescences than plants of 'Daybreak Dark Bronze'.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant. The photograph is a side perspective view of a typical flowering plant of 'Fidmerbrobimp' grown in a 19-cm container.

DETAILED BOTANICAL DESCRIPTION

The aforementioned photograph and following observations and measurements describe plants grown during the winter in 19-cm containers in a glass-covered greenhouse in Fareham, Hampshire, United Kingdom and under cultural practices typical of commercial garden *Chrysanthemum* production. During the production of the plants, day and night temperatures ranged from 17° C. to 21° C. and light levels averaged 6,000 lux. Plants were grown under long day/short night conditions for eight weeks (including propagation period) and then grown under short day/long night conditions to induce inflorescence initiation and development. Plants were 14 weeks old when the photograph and detailed description were taken. In the following description, color references are made to The Royal Horticultural Society Colour Chart, Fifth Edition, except where general terms of ordinary dictionary significance are used.

Botanical classification: *Chrysanthemum×morifolium* 'Fidmerbrobimp'.

Parentage:

*Female, or seed, parent.*—Proprietary selection of *Chrysanthemum×morifolium* identified as code number G0004, not patented.

*Male, or pollen, parent.*—Proprietary selection of *Chrysanthemum×morifolium* identified as code number 83524, not patented.

Propagation:

*Type.*—Terminal vegetative cuttings.

*Time to initiate roots, summer.*—About ten days at temperatures about 21° C.

*Time to initiate roots, winter.*—About twelve days at temperatures about 21° C.

*Time to produce a rooted young plant, summer.*—About three weeks at temperatures about 21° C.

*Time to produce a rooted young plant, winter.*—About four weeks at temperatures about 21° C.

*Root description.*—Fine, fibrous; typically light brown in color, actual color of the roots is dependent on substrate composition, water quality, fertilizer type and formulation, substrate temperature and physiological age of roots.

*Rooting habit.*—Freely branching; medium density to dense.

Plant description:

*Plant and growth habit.*—Herbaceous decorative-type garden *Chrysanthemum*; stems upright to outwardly spreading giving a uniformly mounded appearance to the plant; numerous lateral branches and relatively short internodes, dense and full plant form; moderately vigorous to vigorous growth habit.

*Plant height.*—About 23 cm.

*Plant width.*—About 31 cm.

*Main stem diameter.*—About 5 mm.

*Branching habit.*—Freely branching habit; about 16 lateral branches develop after removal of terminal apex (pinching).

*Lateral branches.*—Length: About 9 cm. Diameter: About 3 mm. Internode length: About 9 mm. Strength: Moderately strong. Aspect: About 85° from vertical. Texture: Fine pubescence. Color: Close to 147C.

Leaf description:

*Arrangement.*—Alternate, simple.

*Length.*—About 5.6 cm.

*Width.*—About 4.5 cm.

*Shape.*—Palmately-lobed; roughly ovate with three to five lobes.

*Apex.*—Broadly acuminate to mucronate.

*Base.*—Attenuate.

*Margin.*—Slightly dentate and palmately lobed; sinuses between lateral lobes divergent.

*Texture, upper surface.*—Fine pubescence; slightly rough.

*Texture, lower surface.*—Fine pubescence; veins prominent on lower surface.

*Color.*—Developing leaves, upper surface: Close to 137A. Developing leaves, lower surface: Close to 147B. Fully expanded leaves, upper surface: Close to 137B; venation, close to 138B. Fully expanded leaves, lower surface: Close to 147B; venation, close to 138B.

*Petioles.*—Length: About 2.1 cm. Diameter: About 2 mm. Texture, upper surface: Fine pubescence; slightly rough. Texture, lower surface: Fine pubescence. Color, upper and lower surfaces: Close to 138B.

Inflorescence description:

*Form and flowering habit.*—Decorative-type inflorescence form with ligulate-shaped ray florets; inflorescences borne on terminals above and beyond the foliar plane; disc and ray florets arranged acropetally on a capitulum; freely flowering habit with about 73 inflorescences developing per plant.

*Fragrance.*—Mildly fragrant; pungent, herbaceous.

*Flowering response.*—Mid-season flowering habit, plants exposed to natural season conditions begin flowering in early to mid-September in the United Kingdom; plants flower uniformly and continuously.

*Inflorescence longevity.*—Inflorescences maintain good color and substance for about three to five weeks on the plant; inflorescences persistent.

*Inflorescence buds.*—Height: About 3 mm. Diameter: About 4 mm. Shape: Oblate. Color: Close to 137B.

*Inflorescence diameter.*—About 5 cm.

*Inflorescence height.*—About 1.5 cm.

*Receptacles.*—Height: About 4 mm. Diameter: About 3 mm. Shape: Conical. Color: Close to 145B.

*Ray florets.*—Number of ray florets per inflorescence: About 203 arranged in about ten whorls. Orientation: Initially upright, then about 45° from vertical. Length: About 1.9 cm. Width: About 5 mm. Shape: Ligulate. Apex: Rounded and emarginate. Base: Fused into a short tube. Margin: Entire. Texture, upper and lower surfaces: Smooth, glabrous; double-keeled. Color: When opening, upper surface: Close to N163C; towards the margins, close to 169A. When opening, lower surface: Close to 42B. Fully opened, upper surface: Close to N163C; towards the margins, close to 169A; with development, color becoming closer to N163D. Fully opened, lower surface: Close to 173B; with development, color becoming closer to 173C.

*Disc florets.*—Disc floret development has not been observed on plants of the new *Chrysanthemum.*

*Phyllaries.*—Number of phyllaries per inflorescence: About 24 arranged in about three whorls. Length: About 7 mm. Width: About 3 mm. Shape: Ovate. Apex: Obtuse. Base: Obtuse. Margin: Entire. Texture, upper surface: Smooth, glabrous; waxy. Texture, lower surface: Fine pubescence; waxy. Color, upper surface: Close to 146B. Color, lower surface: Close to 146A.

*Peduncles.*—Length, terminal peduncle: About 5.5 cm. Diameter, terminal peduncle: About 2 mm. Angle: Erect to about 45° from vertical. Strength: Moderately strong; flexible. Texture: Dense pubescence. Color: Close to 138B.

*Reproductive organs.*—Androecium: None observed. Gynoecium: Present only on ray florets. Pistil length: About 4 mm. Stigma shape: Bi-parted. Stigma color: Close to 13A. Style length: About 3 mm. Style color: Close to 160A. Ovary color: Close to 157C.

*Seeds and fruits.*—Seed and fruit production has not been observed on plants of the new *Chrysanthemum.*

Disease & pest resistance: Resistance to pathogens and pests common to *Chrysanthemum* plants has not been observed on plants of the new *Chrysanthemum.*

Garden performance: Plants of the new *Chrysanthemum* have demonstrated good garden performance and to tolerate temperatures from about 0° C. to about 35° C.

It is claimed:

1. A new and distinct *Chrysanthemum* plant named 'Fidmerbrobimp' as illustrated and described.

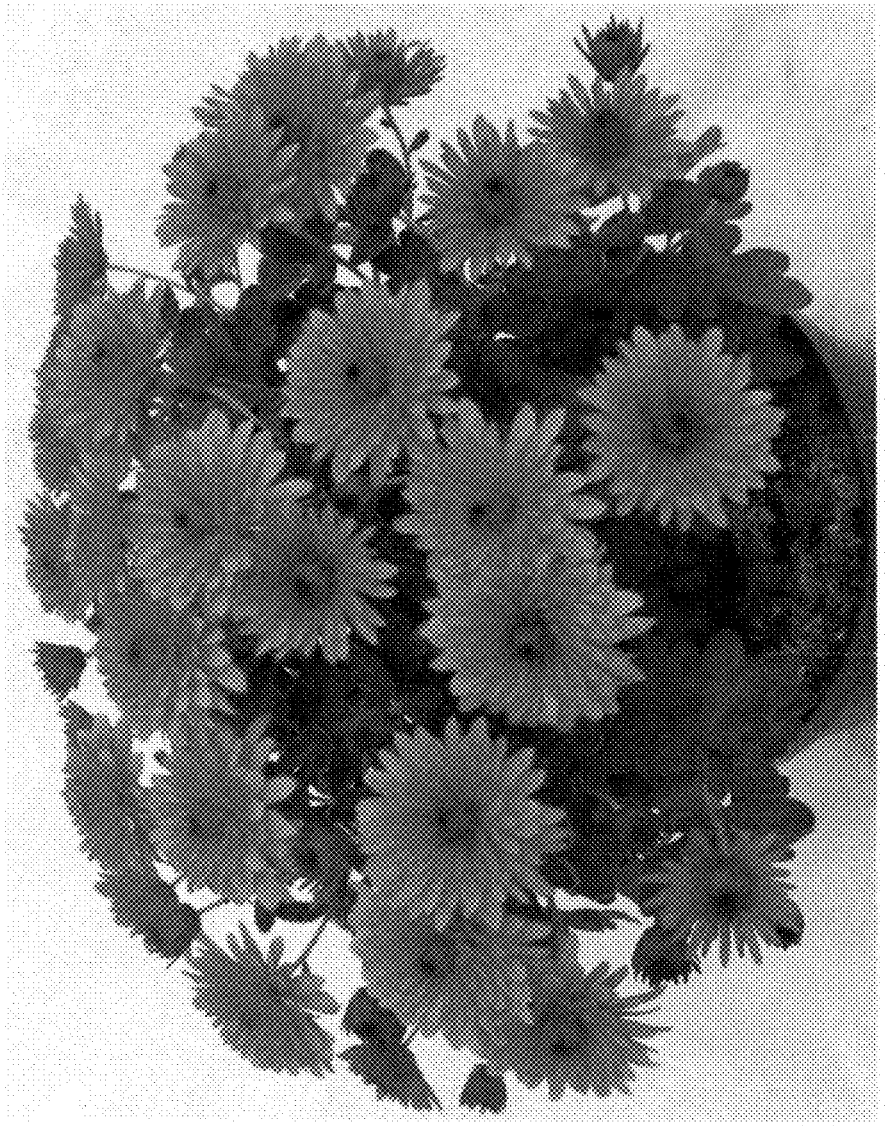

* * * * *